United States Patent [19]

Lattuada et al.

[11] Patent Number: 4,709,819
[45] Date of Patent: Dec. 1, 1987

[54] METHOD FOR PRESERVING PLATED MEDIA AND PRODUCT

[75] Inventors: Charles P. Lattuada, Burlington; Frank R. Gladden, Jr., Mebane, both of N.C.

[73] Assignee: Environmental Diagnostics, Inc., Burlington, N.C.

[21] Appl. No.: 888,521

[22] Filed: Jul. 23, 1986

[51] Int. Cl.$^4$ .................. B65D 85/00; B65B 55/04
[52] U.S. Cl. .................. 206/524.8; 53/426; 53/434; 53/449; 435/297
[58] Field of Search .............. 53/432, 167, 512, 431, 53/425, 433, 426, 434, 474, 449, 479; 435/298, 297, 299; 206/213.1, 484, 524.8, 569

[56] References Cited

U.S. PATENT DOCUMENTS

| | | | |
|---|---|---|---|
| 3,726,057 | 4/1973 | Kemble | 53/425 |
| 3,728,839 | 4/1973 | Glick | 53/434 X |
| 3,751,341 | 8/1973 | Seitz et al. | 435/298 X |
| 4,021,283 | 5/1977 | Weikert | 53/426 X |
| 4,057,951 | 11/1977 | Schneider | 53/512 X |
| 4,099,914 | 7/1978 | Gustafsson et al. | 53/426 |
| 4,262,091 | 4/1981 | Cox | 435/299 X |
| 4,541,224 | 9/1985 | Mugnai | 53/434 |

FOREIGN PATENT DOCUMENTS 77458 4/1983 European Pat. Off. .............. 53/434

Primary Examiner—Robert L. Spruill
Assistant Examiner—Steven P. Weihrouch
Attorney, Agent, or Firm—B. B. Olive

[57] ABSTRACT

A process and package product for preserving bacteriological culture media and gels is based on use of a sterilized air, liquid, and light impervious flexible wall pouch in which a Petri dish or similar device containing the medium or gel is stored and which is heat sealed after being evacuated and flushed with a inert gas to remove oxygen from within the dish and the pouch while in a vacuum chamber.

4 Claims, 2 Drawing Figures

METHOD FOR PRESERVING PLATED MEDIA AND PRODUCT

DESCRIPTION

TECHNICAL FIELD

The invention relates to preserving plated microbiological culture media and a packaged product incorporating such media.

BACKGROUND ART

Since the invention in part relates to vacuum packaging, it is noted that reagents and other laboratory and research products have been vacuum packed. Also noted is the fact that microbiological culture media has been packed in bottles with screw caps and also in flat bottles. Another practice has been to package biological culture media in Petri culture dishes and insert the Petri culture dish in a plastic pouch but with no bactericidal or inert gas treatment of the pouch or use of vacuum sealing after such treatment.

While other methods for preserving and packaging microbiological culture media might be described, it is believed the above is sufficient to describe the general state of the art. Further, so far as applicants are aware all known methods for preserving plated media typically provide a shelf life ranging under refrigeration, between a relatively few weeks and at the most approximately five to six months. There has been a long-standing need for a method of preserving microbiological culture media which does not require refrigeration and which does allow the culture media to be stored at room temperature without refrigeration and without dehydration and/or deterioration of the medium.

The present invention is deemed to be applicable to all agar media and gels prepared in Petri dishes or similarly constructed containers such as plastic containers manufactured for the purpose of containing an agar or gel medium for the purpose of growing microorganisms or demonstrating a microbial reaction such as agar immuno-diffusion. The achieving of an improved process for preserving plated media and gels and improved packaging for such media and gels thus becomes the primary object of the invention. Other objects will appear as the description proceeds.

DISCLOSURE OF INVENTION

The invention is based on storing microbiological media and gels in a conventional, disposable, sterile Petri dish or similar container having optical clarity and a loose fitting cover and typically formed of polystyrene. An air, liquid and light impervious paper-plastic film-foil pouch in which the Petri dish containing the media is stored is first treated with a sterilizing agent. The Petri dish or similar container containing the medium or gel is then inserted into the pouch. The pouch is next evacuated to remove oxygen from both the pouch and the Petri dish. Next, an inert gas is introduced and the vacuum is relieved. The pouch is next heat sealed while remaining under partial vacuum. The chamber vacuum is then relieved which collapses the pouch around the product to produce the packaged product of the invention.

BEST MODE FOR CARRYING OUT THE INVENTION

Figure 1:
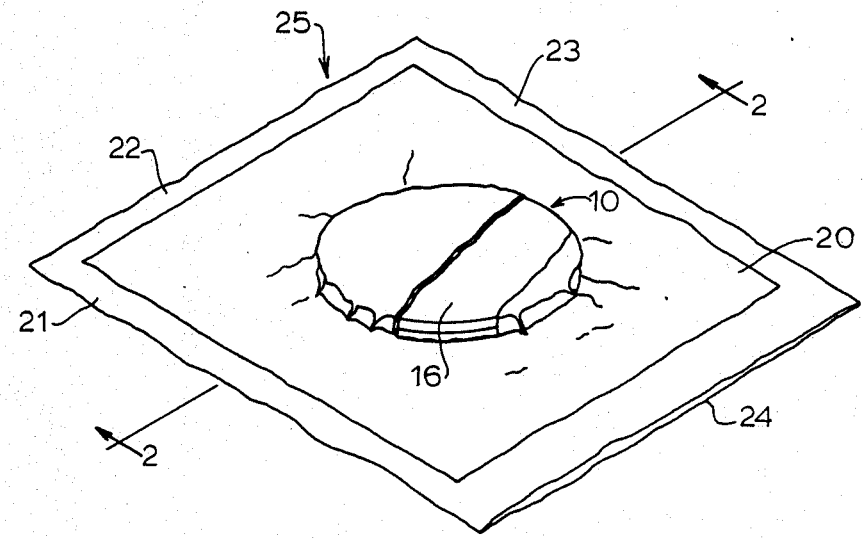
FIG. 1 is a perspective view of a vacuum packaged foil pouch a microbiological medium in a Petri dish according to invention with certain parts broken away for illustration.
Figure 2:
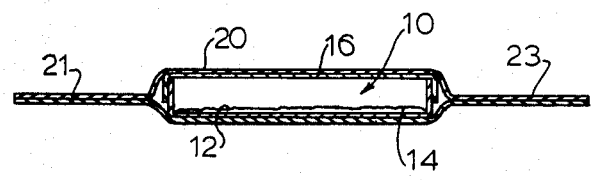
FIG. 2 is a cross-sectional view taken on line 2—2 of FIG. 1.

Making reference to the drawings, the microbiological medium or gel to be preserved is preferably placed in a disposable, sterile, Petri dish 10 or similar container, typically formed of polystyrene, having optical clarity and sufficient strength to withstand the vacuum sealing process of the invention without breakage. The Petri dish 10 or similar container receives the microbiological medium or gel 12 to be preserved and in the case of the Petri dish comprises the typical round bottom dish 14 in which the medium 12 is stored and a loose fitting top cover 16.

An air, liquid, and light impervious pouch 20 is employed and which is typically formed of a plastic-paper-foil laminate with three sealed sides 21, 22 and 23 and an initially unsealed, open end 24 through which the Petri dish 10 or similar container to be stored is inserted. Pouch 20 is initially treated with a bactericidal agent such as an Alcide ABQ (trademark) aerosol so as to chemically sterilize the interior of the pouch 20. The Alcide ABQ aerosol is made by Alcide Corporation of Norwalk, Conn. 06851, and comprises a two part product presently known as a potentiated chlorine-dioxide. One part by volume comprises sodium chlorite operative as a disinfectant and the other equal part by volume comprises an activator of 0.6% organic acid, e.g., lactic acid. The parts are mixed prior to use. Other bactericidal agents deemed suited for the invention include acidified alcohol and other liquid bactericidal agents shown to have no deletrious effect on the product being packaged.

The Petri dish 10 or other similar container containing the medium 12 is next inserted aseptically into the pouch 20 through initially open end 24 and is placed to permit subsequent heat sealing of said open end 24. The pouch 20 is next inserted in a vacuum chamber equipped with a heat sealer in which a pressure of approximately one atmosphere is established to remove oxygen and excess sterilizing agent from both within the pouch and within the Petri dish 10 utilizing the loose fitting cover 16 to effect such removal. The interior surface of pouch 20 is left with a sterilizing coating of the agent. Pouch 20 and the vacuum chamber are next evacuated to a pressure of less than 10 mm of mercury and pouch 20 is then flushed with an inert gas, e.g. nitrogen or carbon dioxide, admitted to the vacuum chamber and pouch and the vacuum is relieved to a pressure of preferably less than 0.6 atmosphere. Because of Petri dish cover 16 or whatever similar container cover is used, having a loose fit on bottom dish 14 of the dish 10, the inert gas also tends to purge the space within the Petri dish 10 or similar container above the medium or gel of oxygen to stop oxidation activity. Next, the pouch is heat sealed at its opening 24 and the vacuum chamber relieved causing the pouch to collapse as indicated in FIG. 1 which produces the packaged product 25 of the invention. Once collapsed, the sterilizing agent on the interior surfaces of the pouch is brought into intimate contact with the exterior surfaces of the dish 10 to effect a further sterilizing action.

An air, liquid, and light impervious paper-polystyrene foil pouch 20 suited to the invention is made by Technipaq, Inc., 980 East Remington Road, Schaumburg, Ill. 60195 and a heat sealer equipped, vacuum packaging machine suited to the invention is made by the Hantover-Turbovac Company, 2548 Campbell Street, Kansas City, Mo. 64141.

Considering that most microbiological culture medium and gels comprise about 98% water by volume, it is noted that with the packaging process of the invention there is substantially no loss of water from the media during its normal shelf life which can be up to as long as twelve months at room temperature whereas in normal packaging of culture media it is typical to experience at least some water loss on a daily basis. It has also been discovered that with respect to some media, e.g. culture media TSA Blood Agar Plates, the lack of oxygen tends to change the color of the medium by darkening the medium. However it is also noted that when the medium is re-exposed to an oxygen atmosphere, there is a rapid transition to the original color of the medium through room oxygen transfer, thus indicating no degradation of the medium even after a long period of shelf storage up to twelve months.

What is claimed is:

1. A vacuum packaging process for preserving a medium in the nature of biological media or gel such that the media or gel can be preserved without dehydration or deterioration and without refrigeration at ambient temperature for a prolonged time period substantially in excess of six months, said process comprising the steps;
   (a) storing the medium to be preserved in a sterile, optically clear, plastic container formed as a petri like dish with a loose fitting cover to permit air flow between the cover and dish and of sufficient strength to withstand without breakage the vacuum pressures of the process;
   (b) preparing a preformed rectangular pouch having air, liquid, and light impervious heat sealble flexible walls with three sides sealed and one end open to receive said container and treating the interior of the pouch with a bactericidal aerosol agent admitted through said open end to sterilize the interior space and to leave interior surfaces of the pouch coated with the agent prior to receiving said container containing said medium, s aid agent being selected to have no deleterious effect on the said media or gel;
   (c) aseptically inserting said container into the pouch through said open end with the said open end remaining open and with said container placed so as to permit subsequent heat sealing of said open end;
   (d) placing said sterilized pouch containing said container containing said medium, said agent being ber having means for confining a gas introduced and retaining a reduction in pressure established therein and other means within said chamber for heat sealing said open end while maintaining a vacuum in said chamber;
   (e) sealing said chamber to provide a gas tight enclosure and reducing the pressure therein to a first level below the external atmospheric pressure;
   (f) during the presence of such reduced pressure at said first level, admitting to said chamber a gas having the characteristic of being inert to said medium;
   (g) allowing said inert gas to flow through said pouch open end into said container;
   (h) flowing said inert gas from said chamber to remove sufficient oxygen to stop oxidation activity in said biological media or gel and to remove excess said inert gas from said container interior, from said pouch and from space within the chamber surrounding said pouch;
   (i) equalizing the pressure within said pouch and within said chamber surrounding said pouch to a second level below atmospheric pressure;
   (j) heat sealing said pouch open end within said chamber during the presence of said second level of pressure; and
   (k) relieving said reduced pressure in said chamber to bring the chamber pressure to the level of atmospheric pressure and allowing said pouch walls to collapse around said container and bring the interior surfaces of said pouch sterilized and coated by said agent into intimate contact with the exterior surfaces of said container.

2. The process of claim 1 wherein:
   (a) said inert gas comprises a gas selected from the group consisting of nitrogen and carbon dioxide;
   (b) oxygen andthe excess of said inert gas is removed by establishing a vacuum at said first level of approximately one atmosphere in said chamber;
   (c) said inert gas is admitted during a vacuum established at said second level of approximately 0.6 atmosphere in said chamber; and
   (d) said pouch comprises a pouch formed with a paper-polystyrene-foil wall construction.

3. A packaged medium product made by the process of claim 1 and storable without refrigeration at ambient temperature for a prolonged time period substantially in excess of six months without dehydration or deterioration of said media or gel.

4. A packaged medium product made by the process of claim 2 and storable without refrigeration at ambient temperature for a prolonged time period substantially in excess of sixe months without dehydration or deterioration of said media or gel.

* * * * *

UNITED STATES PATENT AND TRADEMARK OFFICE
CERTIFICATE OF CORRECTION

PATENT NO. : 4,709,819

DATED : December 1, 1987

INVENTOR(S) : Charles P. Lattuada & Frank R. Gladden, Jr.

It is certified that error appears in the above-identified patent and that said Letters Patent is hereby corrected as shown below:

Column 1, line 68, insert --containing-- after "pouch".

Column 2, line 1, insert --the-- after "to".

Column 3, line 53-54, cancel ", said agent being ber" and substitute --in a vacuum chamber--.

Column 4, line 52, correct "sixe" to read --six--.

Signed and Sealed this

Tenth Day of May, 1988

Attest:

DONALD J. QUIGG

Attesting Officer

Commissioner of Patents and Trademarks